United States Patent [19]
Gu et al.

[11] Patent Number: 5,035,859
[45] Date of Patent: Jul. 30, 1991

[54] CONTACT LENS DISINFECTING SYSTEM

[75] Inventors: Ben Gu, Evanston; Kenneth E. Bliznik, Lansing; Helmut K. Singer, Lincolnshire; Sharon M. Ward, Forest Park, all of Ill.

[73] Assignee: Schering Corporation, Kenilworth, N.J.

[21] Appl. No.: 439,769

[22] Filed: Nov. 21, 1989

[51] Int. Cl.$^5$ ..................... A61L 2/18; C07D 207/26
[52] U.S. Cl. ...................................... 422/28; 548/543
[58] Field of Search ......................... 422/28; 514/424; 548/543

[56] References Cited

U.S. PATENT DOCUMENTS 4,013,576  3/1977  Loshaek .............................. 422/28
4,719,287  1/1988  Login et al. ........................ 424/115
4,782,078  11/1988 Crawford et al. .................. 548/543
4,828,569  5/1989  Heath et al. ....................... 252/153
4,836,986  6/1989  Ogunbiyi et al. ................... 422/28

Primary Examiner—Robert J. Warden
Assistant Examiner—Howard Hampel
Attorney, Agent, or Firm—Warrick E. Lee, Jr.

[57] ABSTRACT

Contact lenses are disinfected by utilizing an N-alkyl-2-pyrrolidone as the microbicide. The efficacy of prior art microbicides such as chlorhexidene gluconate are enhanced by the addition of the pyrrolidones of this invention. The pyrrolidones suitable for use in the practice of this invention are the $C_8$–$C_{20}$ N-alkyl-2-pyrrolidones. Preferably the alkyl moiety is octyl, decyl or dodecyl. The pyrrolidones can be utilized in solution or made available as a water soluble tablet.

19 Claims, No Drawings

CONTACT LENS DISINFECTING SYSTEM

FIELD OF INVENTION

This invention relates to a system for disinfecting contact lenses. In particular it relates to a method for disinfecting contact lenses utilizing an N-alkyl pyrrolidone.

BACKGROUND OF THE INVENTION

Contact lenses require frequent cleaning in order to remove deposits, the source of which is generally tear fluid. In addition to cleaning it is necessary to disinfect contact lenses to reduce the risk of infection. A common method of disinfecting contact lenses is to contact them with a three percent solution of hydrogen peroxide.

Prior art methods for carrying out the disinfecting process is first to clean and rinse the lenses and then to immerse them in an aqueous three percent solution of hydrogen peroxide for about 10 minutes. The lens is then treated for about 10 minutes to reduce residual hydrogen peroxide absorbed therein to a level which is non-toxic and not irritating to the eye. A prior art method for reducing residual hydrogen peroxide comprises chemical reduction by immersing the lens in an aqueous neutralizing solution followed by rinsing with isotonic saline. While neutralization has been accomplished in numerous ways in the prior art, one approach is to place the lenses in a container of saline solution having a plastic disc coated with catalytic platinum for about four hours. Other methods used for neutralizing residual peroxide include immersion of the lens in an aqueous isotonic saline containing catalase or thiosulfate, bisulfite and pyruvate salts.

British patent number 2,144,875A (British '875) discloses a process for the oxidative cleansing of contact lenses which is similar to that utilized in cleansing dentures. An oxidative cleansing solution is prepared using a solid material which gives chemical release of hydrogen peroxide. Illustrative examples of solid materials giving chemical release of hydrogen peroxide include percarbonates, persulfates, perborates, peroxyhydrates and other per salts of alkali metals and other anions. In one embodiment the solid material is mixed with anhydrous citric acid, polyvinylpyrrolidone and powdered sodium lauryl sulfate. The mixture is tabletted by compression in a conventional tabletting equipment.

British patent number 1,221,038 (British '038) discloses an effervescent medicinal tablet which comprises adipic acid and sodium bicarbonate. An alleged advantage of the use of adipic acid is that no lubricant is required in the tabletting process.

U.S. Pat. No. 4,414,127 discloses a method of utilizing a transition metal catalyzed peroxide solution to cleanse contact lenses. The preferred metal is copper. While the peroxide is generally provided in a solution form it can be made available as a tablet or powder. The hydrogen peroxide source can be a hydrogen peroxide solution, urea peroxide, sodium percarbonate or sodium perborate. The solution contains an imadazoline surfactant or a cocohydrolized animal protein anionic surfactant. While the concentration of hydrogen peroxide in solution is disclosed to encompass the range 0.1 to 15% by weight/volume. The preferred range is 0.5 to 10% (w/v). Most preferably, the peroxide concentration is 1%.

U.S. Pat. No. 4,401,582, discloses a method for ambient temperature or cold disinfection of soft contact lenses utilizing ascorbic acid for killing bacteria.

A method for disinfecting contact lenses is disclosed wherein an ene-diol composition is utilized in conjunction with copper ion. See for example U.S. Pat. Nos. 4,490,389; 4,581,472 and 4,581,379. The preferred ene-diols are dihydroxyfumaric acid, dihydroxymaleic acid, reductic acid and ascorbic acid.

U.S. Pat. No. 4,312,833, discloses a sterilizing solution for disinfecting contact lenses comprising (a) an alkali metal of formic acid, and (b) an iodophor selected from the group consisting of complexes of iodine with hydrophilic polymer and non-ionic surface active agent.

SUMMARY OF THE INVENTION

It surprisingly has been found that aqueous solutions of N-alkyl-2-pyrrolidone are effective as cleaning/disinfecting solutions for contact lenses. These solutions posses excellent antimicrobial activity and have low occular irritation.

DETAILED DESCRIPTION OF THE INVENTION

This invention relates to systems for cleaning and disinfecting contact lenses comprising aqueous solutions of N-alkyl-2-pyrrolidone having the general formula:

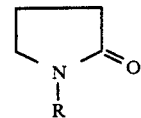

where R is a $C_8$–$C_{20}$ alkyl moiety. Preferably R is an alkyl group of 8 to 12 carbon atoms. These compounds are available from GAF Corp., N.J., and are sold under its trademark Surfadone.

While the N-alkyl-2-pyrrolidones useful in the practice of this invention can be used as the sole antimicrobial agent, they can be used in conjunction with other surfactants including non-ionic, cationic, anionic or amphoteric surfactants. Illustrative non-limiting examples of such surfactants are Pluronic ®, an ethylene oxide/propylene oxide non-ionic block copolymer; Tetronic ®, an alkoxylated diamine, each nitrogen being substituted with an ethylene oxide/propylene oxide copolymer; Igepals ®, a class of alkyl phenoxyethylene-ethoxy ethanol non-ionic oligomers; Hamposyl, an alkyl sarcosinate which is anionic; Avenol ®, an alkyl polyether sulfonate, an anionic surfactant; Miranol ® H2M, an amphoteric carboxylated imadazolide and Deriphate ®, an amphoteric alkyl-$\beta$-iminodipropynate; Those skilled in the art having access to this disclosure will readily be able to ascertain other suitable surfactants from McCutcheon's Detergents and Emulsifiers, North American Edition, McCutcheon Division, MC Publishing Co,., Glen Rock, N.J. The nonionic surfactants can be employed as buffer enhancer as well as cleaning and disinfecting agents. When employed as a buffer enhancer the nonionic surfactants are utilized at about 0.0001 to about 5.0 weight percent of solution. Similarly the pyrrolidones of this invention can be utilized in conjunction with inorganic compounds commonly used in contact lens solutions. Illustrative non-limiting examples of such inorganic compounds include sodium chloride, borates, phosphates, disodium edetate, etc. Conventional buffers can be used in the CL solutions of this invention. Illustrative examples of these buffers are sodium or potassium citrate, citric acid, sodium bicarbonate, as well as mixed phosphate buffers such as $Na_2HPO_4$, $NaH_2PO_4$ and $KH_2PO_4$. Generally the buffers can be used in amounts ranging from about 0.05 to about 2.5 weight percent of the solution, preferably about 0.1 to about 1.5 weight percent.

The antimicrobial effectiveness of prior art microbicides can be enhanced by incorporating the N-alkyl-2-pyrrolidones of this invention into prior art compositions. Illustrative non-limiting examples of prior art microbicides which are compatible with the pyrrolidones of this invention include chlorhexidine gluconate, polyguanidines, polyquats and ascorbic acid. Illustrative of the polyguanidines is polyhexamethylene guanide; see U.S. Pat. No. 4,758,595 incorporated herein by reference. Illustrative of the polyquats useful as microbicides is α-4-[-tris(2-hydroxyethyl) ammonium chloride-2-butenyl] poly[1-dimethylammonium chloride-2-butenyl]-w-tris (2-hydroxyethyl) ammonium chloride; see U.S. Pat. No. 4,407,791 incorporated herein by reference. Other suitable germicides include sorbic acid, thimerosal, 1,5 pentanediol and water soluble salts such as gluconate, isothionate, formate, acetate, dimethanesulfonate, etc. Generally the microbicides can be utilized at about 0.00001 to about 0.003 weight percent.

Suitable sequestering agents can be included in the compositions of this invention. Illustrative non-limiting examples of such sequestering agents are ethylene diaminetetraacetic acid, gluconic acid, citric acid, tartaric acid, and their water soluble salts.

In order to have the desired antimicrobial effectiveness the N-alkyl-2-pyrrolidones of this invention can be utilized at concentration in aqueous solution of about 0.0001% to about 0.5% by weight of the solution. Preferably the concentration in the disinfecting solution is about 0.001% to about 0.2% by weight. When used as a preservative the concentration of N-alkyl-2-pyrrolidone in a lens cleaning solution is about 0.001% to about 0.1% by weight; preferably about 0.0002 to about 0.05%.

In the practice of this invention the cleaning and disinfecting agent is generally supplied as an aqueous solution or a water soluble tablet or powder. After cleaning and disinfecting the lens it may be stored in the pyrrolidone solution. The N-alkyl-2-pyrrolidone of this invention, however, can be incorporated into tablets together with other components to enhance antimicrobial activity. If desired, various excipients can be added to the N-alkyl-2-pyrrolidone including salts, buffers, sequestering agents and stabilizers so that the disinfecting solution will have the proper pH and tonic value. A particularly advantageous composition comprises the N-alky-2-pyrrolidone and a sodium lauryl sarcosinate or Chlorhexidine gluconate. The sarcosinate can be utilized at about 0.1% to about 0.03% by weight of solution. The chlorhexidene gluconate can be utilized at about 0.00005 to about 0.01% by weight of solution. Additionally, cleansing agents to aid in cleansing the lens can be included. Illustrative, non-limiting examples of such cleansing agents are sodium lauryl sulfate, alkyl aryl polyether alcohols, monocarboxylated, dicarboxylated or sulfonated fatty acid substituted imadazoline surfactants and EDTA. Optionally, a tonicity salt may be included in the composition.

Where the composition is supplied in tablet or powdered form the concentration of components is adjusted so that when used in the quantity of desired solution the concentration of individual components in solution is within the range described above. Suitable tabletting aids include polyethylene glycol waxes, stearic acid and alkali metal stearates.

Before disinfecting with the composition of this invention, it is preferable to clean the lens of any deposits from the eye by placing a few drops of saline solution on the lens and rubbing it between the thumb and index finger. Alternatively, one of the many commercial contact lens cleaners may be used. To disinfect a contact lens one immerses the lens in an aqueous liquid and adds a tablet containing the pyrrolidone of this invention to the aqueous liquid. The lens is allowed to remain in the resulting solution for a time sufficient to disinfect the lens.

In one aspect of the invention the method for disinfecting contact lenses comprises the steps of:

(1) Immersing a contact lens in a liquid comprising water or a saline solution having an N-alkyl-2-pyrrolidone concentration of about 0.001 to about 0.2 percent by weight for a time sufficient to disinfect the lens; and (2) wearing the lens on the eye with or without subjecting the lens to further treatment.

While in a preferred embodiment the lens is rinsed with sterile saline solution before applying to the eye, the pyrrolidones of this invention are non-irritating and further treatment is not necessary.

Any suitable container may be utilized to carry out the disinfecting process of this invention. Illustrative of such containers are lens cases and containers of the type described in British patent 2,144,875A. That container consists of a cell comprising a base and a cover which can be secured together with a fluid tight joint, the base having a rounded internal surface, and an indicator it indicate the liquid level appropriate for use in the cell. Another embodiment of the invention comprises a kit comprising:

(a) a container calibrated to indicate a specific volume of aqueous liquid;

(b) a cover for the calibrated container having means for holding at least one contact lens at a position below the level of the liquid; and (c) at least one dose of solid material, which when dissolved in the specific amount of liquid in the calibrated container results in an N-alkyl-2-pyrrolidone concentration in the liquid of about 0.001 to about 0.2% by weight.

For testing disinfecting efficiency microorganisms are added to a sterile test tube filled with saline solution to yield a colony of about $10^6$ Colony Forming Units (CFU) per milliliter. The concentration of CFU per ml in the vial is determined shortly before the disinfection formulation is added.

Shortly thereafter, aliquots are withdrawn from the vial at desired time intervals in accordance with the Testing Guidelines. These methods were employed with the formulations of the following examples.

EFFICACY TESTS

The antimicrobial activity of the formulations of this invention were tested against various micro-organisms as required by the Testing Guidelines for Class III Contact Lens Solutions issued by the Food and Drug Administration on July 15, 1985, modified with respect to the concentration of the bacterial load. The test requires about 500,000 to 2,000,000 CFU/ml of bacteria. The modification noted below with respect to bacterial load was used.

Various concentrations of N-alkyl-2-pyrrolidones were prepared in a buffered saline solution. About 100,000 to 1,000,000 CFU/ml of bacteria were added. After exposure to these solutions, the surviving cells were determined at periodic time intervals. The results are shown in Table I.

TABLE I

| Example # | N-alkyl-2-pyrrolidone Alkyl | Conc. % | C. Albicans Log Reduct. | Hours for Kill |
|---|---|---|---|---|
| 1 | N-Octyl | 0.1 | 5.5 | 0.2 |
| 2 | N-Octyl | 0.05 | 5.6 | 2.0 |
| 3 | N-Decyl | 0.015 | 5.9 | 0.2 |
| 4 | N-Dodecyl | 0.015 | 5.7 | 0.5 |

Solutions prepared in the manner of Examples 1–4 were tested using a fixed exposure time of four (4) hours. The results are shown in Table 2.

TABLE II

| Example # | N-alkyl-2-pyrrolidone Alkyl | Conc. % | C. Albicans Log Reduct. | Hours for Kill |
|---|---|---|---|---|
| 5 | N-Octyl | 0.025 | 0.9 | 4.0 |
| 6 | N-Decyl | 0 0050 | 2.3 | 4.0 |
| 7 | N-Dodecyl | 0.0025 | 5.0 | <4.0 |

It is evident from the data of Examples 1–7 that all of the pyrrolidones tested are effective microbicides.

A standard CL-solution preserved with chlorhexidine was used as a control to demonstrate the enhanced effect which can be achieved utilizing the pyrrolidones of this invention. N-octyl-2-pyrrolidone was added at the 0.02 wt. % level to the standard solution. The solutions were tested against each other using C. albicans. The quantity of each component is shown in weight percent based on the solution. The results are shown in Table III. Example 8 is a formulation for a known CL-solution and is used as a comparison for the Surfadone ® containing composition.

TABLE III

| COMPONENT | EXAMPLE 8 | EXAMPLE 9 |
|---|---|---|
| N-octyl pyrrolidone | — | 0.02 |
| Chlorhexidine gluconate | 0.003 | 0.001 |
| Hamposyl L-95[1] | 0.05 | 0.05 |
| Sodium chloride | 0.66 | 0.66 |
| Sodium borate | 0.052 | 0.052 |
| Boric Acid | 0.50 | 0.50 |

TABLE III-continued

| COMPONENT | EXAMPLE 8 | EXAMPLE 9 |
|---|---|---|
| Water | q.s. | q.s. |

[1]Hamposyl L-95 is a sodium lauryl sarcosinate manufactured by W. R. Grace & Co.

| Microbial Activity against C. Albicans | EXAMPLE 8 | EXAMPLE 9 |
|---|---|---|
| Log Reduction | 1.2 | 5.5 |
| Hours for Kill | 4.0 | <4.0 |

It is evident from Examples 8 and 9 that the addition of the pyrrolidone results in a substantially improved microbe kill as compared to that achieved with the control.

EXAMPLE 10–13

Various solutions were prepared to demonstrate the effectiveness of the pyrrolidones of this invention against various bacteria. Isotonic saline was used as the solvent. The formulations and results obtained are shown in Table IV.

TABLE IV

| EXAMPLE # | Composition | 4 Hours Logarithmic Reduction[4] | | | |
|---|---|---|---|---|---|
| | | C. alb. | P. aer. | S. epi. | A. fum. |
| 10 | 0.01% N-Decyl[1] 0.1% EDTA[2] 0.0005% Chl. hex.[3] | >5.30 | 1.07 | 1.98 | 2.03 |
| 11 | 0.01% N-Decyl 0.1% EDTA 0.0002% Chl. hex. | >5.20 | 0.87 | 1.96 | 2.26 |
| 12 | 0.01% N-Decyl 0.1% EDTA 0.0001% Chl. hex. | >5.26 | 1.19 | 2.35 | 2.48 |
| 13 | 0.01% N-Decyl 0.1% EDTA 0.00005% Chl. hex. | >5.30 | 2.28 | >4.90 | 2.51 |

[1]N-Decyl - N-decyl-2-pyrrolidone
[2]EDTA - disodium (ethyleneddinitrilo) tetraacetic acid
[3]Chl. Hex - Chlorhexidine gluconate
[4]C. alb - Candida albicans ATCC# 10231
P. aer - Psuedomonas aeruginosa ATCC# 15442
S. epi - Staphylococcus epidermidis ATCC# 17917
A. fum - Aspergillus fumigatus ATTCC# 10894

EXAMPLES 14–19

The experiments of Examples 10–13 were repeated with modifications in the formulations and using S. mar and A. nig. as additional bacteria to be tested and Surfadone LP-300 (N-dodecyl-2-pyrrolidone) as the pyrrolidone. Isotonic saline was used as the solvent.

TABLE V

| EXAMPLE # | Composition | 4 Hours Logarithmic Reduction[1] | | | | |
|---|---|---|---|---|---|---|
| | | C. alb. | P. aer. | S. mar. | S. eip. | A. nig. |
| 14 | 0.0025% LP-300 0.05% ETDA 0.005% Chl. hex. | >4.78 | >5.00 | >5.78 | 3.22 | >4.90 |
| 15 | 0.0025% LP-300 0.05% ETDA 0.0005% Chl. hex. | >4.78 | >5.00 | 2.80 | >5.15 | 4.90 |
| 16 | 0.0025% LP-300 0.05% ETDA 0.00005% Chl. hex. | >5.00 | >4.90 | 1.62 | >5.00 | 2.36 |
| 17 | 0.0025% LP-300 0.005% Chl. hex. | >4.90 | >5.00 | >5.78 | >5.00 | >4.78 |
| 18 | 0.0025% LP-300 0.0005% Chl. hex. | >4.78 | >4.90 | 2.57 | >5.00 | >4.78 |
| 19 | 0.0025% LP-300 | >4.78 | >4.78 | 1.91 | >5.08 | 2.75 |

TABLE V-continued

| EXAMPLE # | Composition | 4 Hours Logarithmic Reduction[1] | | | | |
|---|---|---|---|---|---|---|
| | | C. alb. | P. aer. | S. mar. | S. eip. | A. nig. |
| | 0.00005% Chl. hex. | | | | | |

[1] S. mar. - Serratia marcescens ATCC# 14014
A. nig. - Aspergillus niger ATCC# 16404

As is evident from the data, reducing the EDTA content or Chl. hex content have a minor effect on effectiveness for all but S. mar. and A. nig.

EXAMPLES 20-27

Tablets were prepared using the formulations shown below and tested against C. albicans. each tablet was adjusted to a weight of 60 mg. by the addition of adipic acid and sodium carbonate in a 2/1 ratio. The ratio of these components will depend on the pH desired. Addition of the acid and carbonate results in an effervescent tablet. The tablet was dissolved in 7.5 ml. of isotonic saline solution for the tests. The results are shown in Table VI.

TABLE VI

| Example # | Ingredient[1] (mg.) | Logarithmic Reduction | |
|---|---|---|---|
| | | 1 Hour | 4 Hours |
| 20 | 22 S. perb. 2 LP-100 | >5.45 | |
| 21 | 22 S. perb. 1 N-Decyl 1 Hamposyl | | >5.75 |
| 22 | 1 N-Decyl 15 Tet. 908 | >4.90 | |
| 23 | 1 N-Decyl 7.5 Hamposyl | | >5.26 |
| 24 | 1 N-Decyl Der. 160 | | >5.20 |
| 25 | 11 S. Perb. 1 LP-300 7.5 Hamposyl | >5.41 | |
| 26 | 11 S. Perb. 0.75 LP-300 7.5 Hamposyl 11 S. Perb. 1 LP-300 | | >5.30 |
| 27 | | | >5.00 |
| | 7.5 Hamposyl | | |

[1] Units - mg.
Hamposyl - Sodium lauryl sarcosinate
Tet. 908 - alkoxylated diamine
Der. 160 - Sodium N-coco-aminopropynate
S. perb. - Sodium perborate

EXAMPLES 28-35

A trifunctional tablet was prepared using the formulations shown in Table VII. These formulations were tested against C. albicans. Comparison tests were run using two commercial lens care solutions, HYDROCARE ® (Alergan) and Improved Renau ® (Bausch and Lomb). Each tablet was brought up to a weight of 60 mg. by adding adipic acid and sodium carbonate in a ratio of about 1/1 to about 2/1, making the tablet an effervescent tablet. The tablet was dissolved in 7.5 ml. of isotonic saline for the tests.

Cleaning efficiency was determined by first soaking the lens in a Lysozyme solution and measuring absorption using a U. V. spectrophotometer (280 nm). The lens was then soaked in the CL solution for four hours. After shaking 20 times the lens was removed from the solution and its absorption redetermined. Cleaning efficiency was determined from the difference in initial and final spectrophotometer readings.

TABLE VII

| EXAMPLE # | Component[1] (mg.) | Osmolarity mOsm/kg $H_2O$ | pH | Log Reduction (4 Hours) | Cleaning Efficacy |
|---|---|---|---|---|---|
| 28 | 11 S. Perb. 2 Cosmocil 7.5 Hamposyl | 416 | 6.0 | >5.26 | 8% |
| 29 | 11 S. Perb. 1 LP-300 7.5 Hamposyl | 422 | 6.9 | >5.41 | 8% |
| 30 | 11 S. Perb. 0.75 LP-300 4 Hamposyl | 418 | 7.0 | >5.30 | 10% |
| 31 | 0.75 LP-300 1.5 Hamposyl | 412 | 7.6 | >5.0 | 13% |
| 32 | 0.38 LP-300 0.75 Hamposyl | 414 | 7.6 | >5.08 | 7% |
| 33 | 0.75 CAE 3.75 SDS | 393 | 7.3 | 3.15 | 6% |
| 34 | HYDROCARE ® | 311 | 8.2 | | 3% |
| 35 | Improved | 282 | 7.3 | 2.25 | 4% |

[1] Cosmocil - Polyhexamethylene biguanide hydrochloride
CAE - DL-Pyrrolidone carboxylic acid salt of N-cocoylarginine ethyl ester
SDS - Sodium dodecyl sulfate It is evident from the data that not only do the compositions of this invention show improved bactericidal activity, but that they result in greater cleaning efficacy.

What is claimed is:

1. A method for disinfecting contact lenses which comprises contacting the lenses with an aqueous solution comprising an N-alkyl-2-pyrrolidone, where the alkyl group of the pyrrolidone is a $C_8-C_{20}$ alkyl moiety.

2. The method according to claim 1 wherein the alkyl moiety is a $C_8$–$C_{12}$ moiety.

3. The method according to claim 1 wherein the alkyl moiety is octyl, decyl or dodecyl.

4. The method according to claim 1 wherein the aqueous solution is an isotonic saline.

5. The method according to claim 1 wherein the concentration of pyrrolidone in solution is about 0.001% to about 0.2% by weight of solution.

6. The method according to claim 1 wherein an additional microbicide is included in the solution.

7. The method according to claim 6 wherein the microbicide is chlorhexidene gluconate.

8. The method according to claim 1 wherein sodium lauryl sarcosinate is included in the solution.

9. A kit for disinfecting a contact lens which comprises:
(a) a container calibrated to contain a specific amount of aqueous liquid;
(b) a cover for said container;
(c) means for holding at least one contact lens immersed in the aqueous liquid;
(d) a unit dose of a tablet comprising an N-alkyl-2-pyrrolidone, wherein said unit dose when dissolved in the specific amount of aqueous liquid causes the liquid to have a concentration of pyrrolidone of about 0.001 to about 0.2% by weight of solution.

10. The kit according to claim 9 wherein the pyrrolidone is a $C_8$–$C_{20}$ alkyl pyrrolidone.

11. The kit according to claim 10 wherein the N-alkyl-2-pyrrolidone is a $C_8$–$C_{12}$ alkyl pyrrolidone.

12. The kit according to claim 10 wherein the alkyl moiety is octyl, decyl or dodecyl.

13. The kit according to claim 12 wherein the unit dose of pyrrolidone includes an organic acid and a solid carbonate.

14. The kit according to claim 13 wherein the organic acid is ascorbic acid, adipic acid, anhydrous citric acid or glutaric acid.

15. The kit according to claim 13 wherein the solid carbonate is sodium carbonate, sodium bicarbonate or potassium carbonate.

16. The kit according to claim 13 wherein a container holding at least one dose of the specific amount of aqueous liquid is included.

17. The kit according to claim 16 wherein the aqueous liquid is preserved saline solution, sterile saline solution, isotonic saline, deionized water, distilled water or mixtures thereof.

18. The kit according to claim 10 wherein an additional microbicide is included.

19. The kit according to claim 9 wherein the unit dose of pyrrolidone is in the form of an effervescent powder.

* * * * *